(12) United States Patent
Lim et al.

(10) Patent No.: US 8,847,767 B2
(45) Date of Patent: Sep. 30, 2014

(54) HEALTH CARE SERVER AND METHOD OF OPERATING THE SAME

(75) Inventors: Joon-Ho Lim, Daejeon (KR); Chan Yong Park, Daejeon (KR); Soo Jun Park, Seoul (KR)

(73) Assignee: Electronics and Telecommunications Research Institute, Daejeon (KR)

( * ) Notice: Subject to any disclaimer, the term of this patent is extended or adjusted under 35 U.S.C. 154(b) by 115 days.

(21) Appl. No.: 13/550,811

(22) Filed: Jul. 17, 2012

(65) Prior Publication Data

US 2013/0154837 A1 Jun. 20, 2013

(30) Foreign Application Priority Data

Dec. 14, 2011 (KR) ........................ 10-2011-0134832

(51) Int. Cl.
*G08B 23/00* (2006.01)

(52) U.S. Cl.
USPC ............... 340/573.1; 340/539.11; 340/825.49

(58) Field of Classification Search
USPC ......... 340/573.1, 531, 539.1, 539.11–539.12, 340/825.49, 5.52, 5.82, 7.58–7.59, 7.6
See application file for complete search history.

(56) References Cited

U.S. PATENT DOCUMENTS

| | | | |
|---|---|---|---|
| 8,380,834 B2 * | 2/2013 | Jeon et al. ...................... 709/223 |
| 2006/0122525 A1 * | 6/2006 | Shusterman .................. 600/513 |
| 2006/0271410 A1 * | 11/2006 | Rosenfeld et al. ................ 705/3 |
| 2007/0285226 A1 * | 12/2007 | Yi ............................ 340/539.12 |
| 2008/0004904 A1 * | 1/2008 | Tran ..................................... 705/2 |
| 2008/0021834 A1 * | 1/2008 | Holla et al. ...................... 705/51 |
| 2009/0157429 A1 * | 6/2009 | Lee et al. .......................... 705/3 |
| 2011/0035627 A1 | 2/2011 | Jeon et al. |
| 2012/0245955 A1 * | 9/2012 | Bari et al. ......................... 705/3 |

FOREIGN PATENT DOCUMENTS

| | | |
|---|---|---|
| KR | 10-2002-0005888 A | 1/2002 |
| KR | 10-2010-0067786 B1 | 6/2010 |

\* cited by examiner

*Primary Examiner* — Daniel Previl

(57) ABSTRACT

The inventive concept relates to a health care system, and more particularly, to a health care server of the health care system and a method of operating the same. The health care server includes a symptom collection module collecting clinical information of patient from a hospital server and health information of patient from an individual health record server; an alarm and reaction rule management module generating an alarm rule on the basis of the clinical information and the health information; and an alarm generation module monitoring the health information or the clinical information and generating an alarm when the monitored health information or the clinical information corresponding to the alarm rule. The health care server can provide a different alarm service to a patient having a different health state with reference to clinical information and health information of each patient.

13 Claims, 5 Drawing Sheets

Fig. 2

Rule 1
{ Disease Code = "Cerebral infarction" &
TOAST Disease Classification = "Cardio-aortic embolism" &
Prescription Code ⊃ "hypoglycemic agent" &
(3 times or more a weak (Glucose AC(Blood Sugar before meals) >= 150mg/dl || Glucose AC < 50mg/dl))
::⇒
(Measure blood sugar again after fasting for 6 hours and after that, talk with a doctor.)
}

Rule 2
{ Disease Code = "Cerebral infarction" &
TOAST Disease Classification = "Small artery occlusion" &
Prescription Code ⊃ "Statin drugs for Hyperlipidemia" &
(3 times or more a weak Total Cholesterol >= 220mg/dl)
::⇒
(If LDL Cholesterol >= 120mg/dl, talking with a doctor)
}

Rule 3
{ Disease Code = "Cerebral infarction" &
(twice or more a weak H-CRL >= 3.0 mg/L)
::⇒
(Hospital visit after talking with a doctor)
}

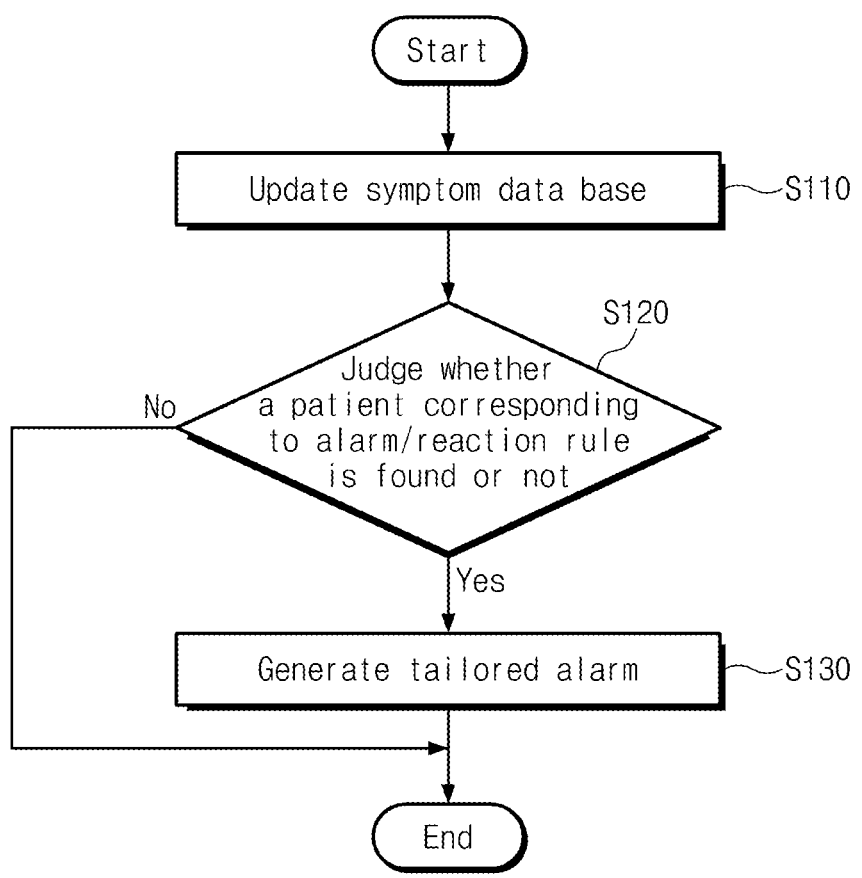

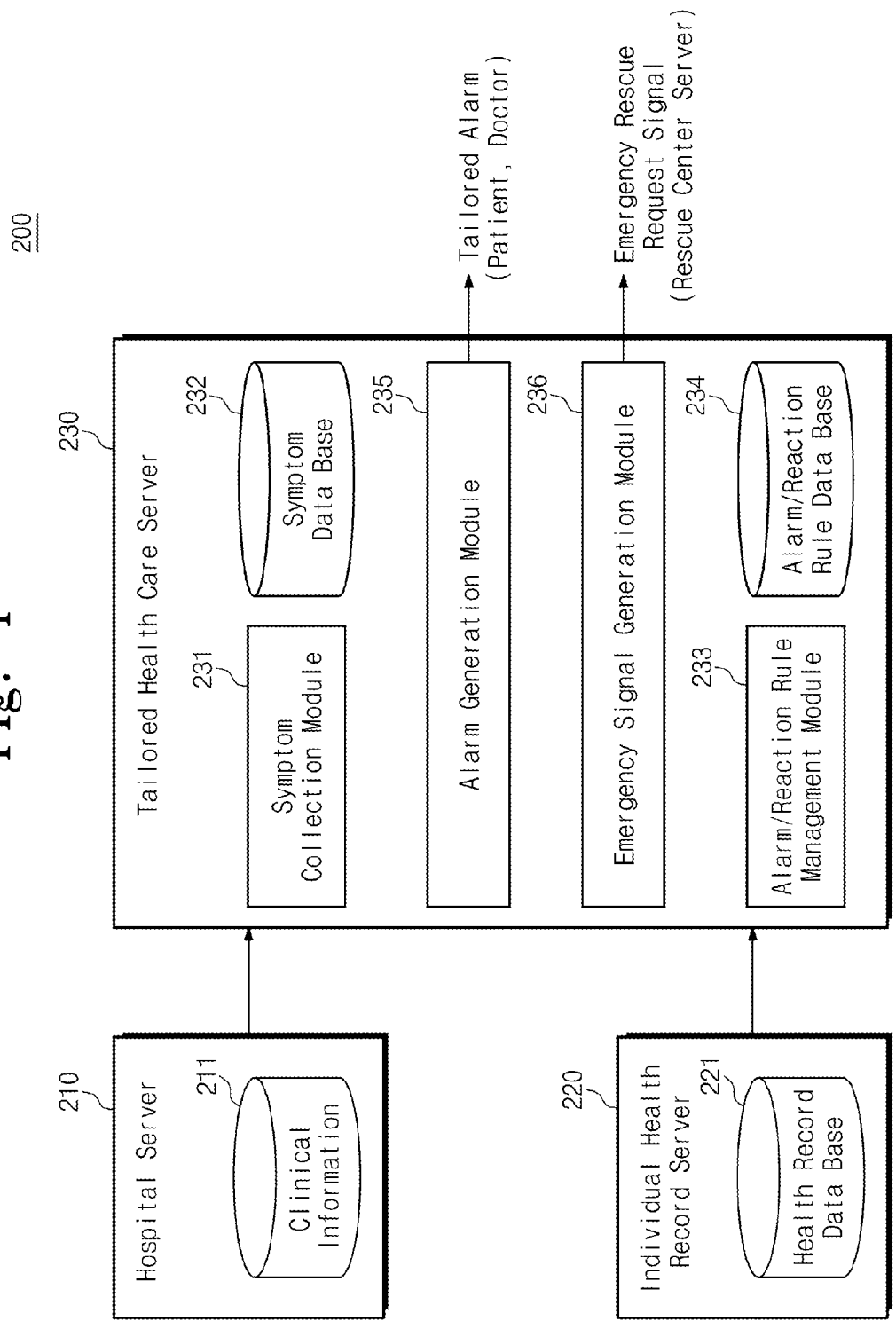

HEALTH CARE SERVER AND METHOD OF OPERATING THE SAME

CROSS-REFERENCE TO RELATED APPLICATIONS

This U.S. non-provisional patent application claims priority under 35 U.S.C. §119 of Korean Patent Application No. 10-2011-0134832, filed on Dec. 14, 2011, the entire contents of which are hereby incorporated by reference.

BACKGROUND

The present inventive concept herein relates to health care systems, and more particularly, to a health care server of health care system and a method of operating the same.

As the standard of living is improved, an interest in health continues to increase. As a smart phone and a tablet PC become popular, an interest in a technology simply checking health information at home or at work also continues to increase.

If the elderly having chronic disease measures health information such as a blood pressure, a blood sugar, etc., there is a technology of informing whether a health of the elderly is well or not according to the previously defined rule. However, in conventional ways, without considering an individual disease and the degree to which the disease is succeeding, whether a health of user is well or not is judged by applying the same rule to all the users.

SUMMARY

Embodiments of the inventive concept provide a health care server. The health care server may include an alarm and reaction rule management module generating an alarm rule on the basis of clinical information of patient collected from a hospital server and health information of patient collected from an individual health record server; and an alarm generation module monitoring health information or clinical information of patient collected from the individual health record server and generating an alarm when the monitored health information or the clinical information of patient corresponding to the alarm rule set in alarm and reaction rule management module.

Embodiments of the inventive concept also provide an operation method of health care server. The operation method may include storing health information received from an individual health record server of patient in a symptom data base; comparing the health information with an alarm rule corresponding to the patient among alarm rules stored in an alarm and reaction rule data base; and generating an alarm when the health information corresponds to the alarm rule of the patient.

BRIEF DESCRIPTION OF THE FIGURES

Preferred embodiments of the inventive concept will be described below in more detail with reference to the accompanying drawings. The embodiments of the inventive concept may, however, be embodied in different forms and should not be construed as limited to the embodiments set forth herein. Rather, these embodiments are provided so that this disclosure will be thorough and complete, and will fully convey the scope of the inventive concept to those skilled in the art. Like numbers refer to like elements throughout.

FIG. 2 is a drawing showing an embodiment of rules defined in a alarm/reaction rule management module.

FIG. 3 is a flow chart illustrating an operation of tailored health care server of health care system of FIG. 1.

FIG. 4 is a block diagram illustrating a health care system in accordance with some other embodiments of the inventive concept.

DETAILED DESCRIPTION OF THE EMBODIMENTS

Figure 1:
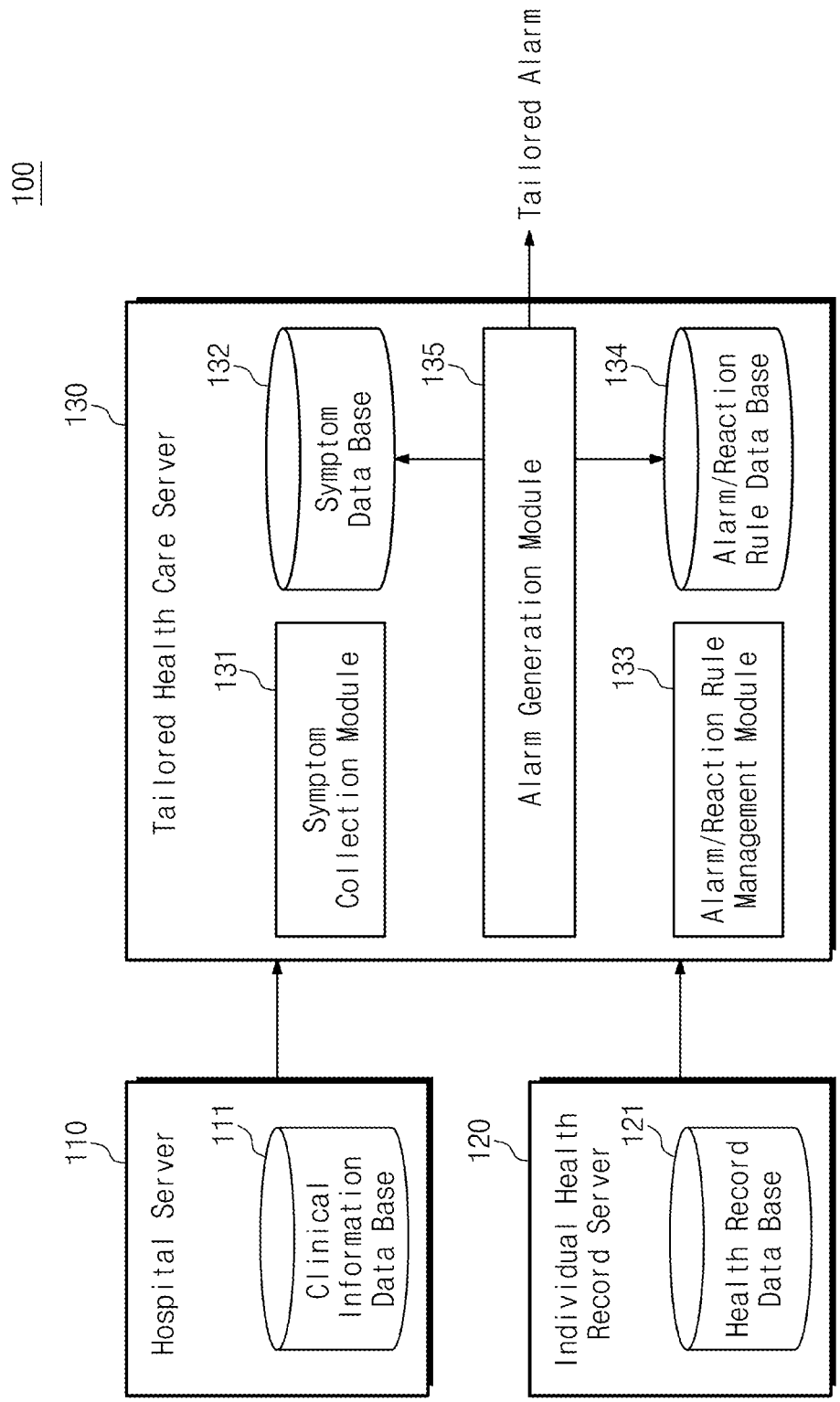
FIG. 1 is a block diagram illustrating a health care system in accordance with some embodiments of the inventive concept.

Embodiments of inventive concepts will be described more fully hereinafter with reference to the accompanying drawings, in which embodiments of the invention are shown. This inventive concept may, however, be embodied in many different forms and should not be construed as limited to the embodiments set forth herein. Rather, these embodiments are provided so that this disclosure will be thorough and complete, and will fully convey the scope of the inventive concept to those skilled in the art. In the drawings, the size and relative sizes of layers and regions may be exaggerated for clarity. Like numbers refer to like elements throughout.

FIG. 1 is a block diagram illustrating a health care system 100 in accordance with some embodiments of the inventive concept. The health care system 100 previously sets a different alarm/reaction rule to a different patient on the basis of clinical information and health information of each patient. Thus, when a health of patient becomes disorder, the health care system 100 can provide a tailored service to a patient. Referring to FIG. 1, the health care system includes a hospital server 110, an individual health record server 120 and a tailored health care server 130.

The hospital server 110 stores clinical information of patient in a clinical information data base 111. The clinical information is a medical record of hospital at which a patient sought medical advice or an electronic medical record (EMR). For example, the clinical information includes a medical record of test result information, prescription information, medical advice information, etc. that a hypertensive, a diabetic patient and a stroke patient had a medical examination at a hospital. The clinical information stored in the hospital server 110 is transmitted to a tailored health care server through a wire/wireless internet or a mobile system.

The individual health record server 120 stores health information of patient measured at home or in a mobile environment in a health record data base 121. When a patient measures health information using a predetermined device at home or in a mobile environment, the measured health information is stored in the health record data base 121 of the individual health record server 120. Health information of patient can be measured by a blood pressure gauge, a blood sugar gauge, a weighing machine, a thermometer, an activity sensor, quantity of motion gauge, a fall sensing device and a taking medicine sensing device.

The tailored health care server 130 receives clinical information of patient and health information of patient from the hospital server 110 and the individual health record server 120 and judges whether or not a health of patient is good according to a state of patient using the clinical and health information. The tailored health care server 130 includes a symptom collection module 131, a symptom data base 132, an alarm/reaction rule management module 133, an alarm/reaction rule data base 134 and an alarm generation module 135.

The symptom collection module 131 receives clinical information of each of patients from the clinical information data base 111 of the hospital server 110. The symptom collection module 131 receives health information of patient from the health record data base 121 of the individual health record server 120. The symptom collection module 131 stores the received clinical information and the received health information in the symptom data base 132.

Data is added to the clinical information when a patient receives a medical treatment. Thus, the clinical information data base 111 and the symptom data base 132 corresponding to the clinical information data base 111 are updated when a patient receives a medical treatment. The clinical information data base 111 and the symptom data base 132 corresponding to the clinical information data base 111 are updated once a month or two months.

Health information can be easily measured at home or in a mobile environment. Thus, the health record data base 121 and the symptom data base 132 corresponding to the health record data base 121 will be frequently updated (e.g., once or twice a day).

The alarm/reaction rule management module 133 generates a rule for judging whether or not a health of patient is good and stores the generated rule in the alarm/reaction rule data base 134. The rule generated from the alarm/reaction rule management module 133 is defined on the basis of clinical information and health information of each patient stored in the symptom data base 132. The rule generated from the alarm/reaction rule management module 133 is tailor-set by a doctor and tailored rule is updated by a doctor's control when a patient visits a hospital or according to a change of patient's condition.

The rule generated from the alarm/reaction rule management module 133 includes a reaction which a patient should perform when the rule corresponds to a corresponding rule. The rule generated from the alarm/reaction rule management module 133 may be defined, for example, like FIG. 2.

Referring to FIG. 2, data regarding to disease code, TOAST disease classification and a prescription code of rule1, rule2 and rule 3 is data collected from the clinical information data base 111 of the hospital server 110. Data regarding to a blood sugar, cholesterol and H-CRP of the rule1, the rule2 and the rule 3 is data collected from the health record data base 121 of the individual health record server 120.

A patient corresponding to the rule 1 has a disease code of "cerebral infarction" and is sick with a disease corresponding to TOAST disease classification of "cardio-aortic embolism". The patient was treated with "hypoglycemic agent" for the corresponding disease. If glucose AC of patient measured at home is more than 150 mg/dl or less than 50 mg/dl, it may be judged that a health of corresponding patient has a problem. In this case, the corresponding patient measures his blood sugar again after fasting for 6 hours and after that, should perform a talking with a doctor.

Referring to FIG. 1 again, the alarm generation module 135 generates a tailored alarm on the corresponding patient when a health of patient has a problem.

The alarm generation module 135 monitors data being input into the symptom data base 132 and checks whether a patient corresponding to the rule stored in the alarm/reaction rule data base 134 is found or not. The alarm generation module 135 accesses to the symptom data base 132 in real time or at intervals of the predetermined time and checks whether a corresponding rule is in the rules stored in the alarm/reaction rule data base 134.

When a patient corresponding to the rule is found, the alarm generation module 135 generates an alarm and transmits the generated alarm to a patient and/or a doctor through SMS, an e-mail and SNS (facebook, tweeter, etc.).

In this case, an alarm generated from the alarm generation module 135 includes information about that a health of corresponding patient has a problem and information a reaction which the corresponding patient should do. If a patient corresponding to the rule 1 is found, the alarm generation module 135 transmits information that the amount of blood sugar has a problem to a patient and transmits information directing that a blood sugar should be measured again after fasting for 6 hours to a patient.

FIG. 3 is a flow chart illustrating an operation of tailored health care server 130 of health care system 100 of FIG. 1. In FIG. 3, for convenience of description, a case that a patient measures health information at home is described as an illustration.

In S110, the symptom data base 132 is updated. That is, when a patient measures his health information using a predetermined device at home, the corresponding information is collected by the symptom collection module 131 and is stored in the symptom data base 132.

In S120, it is judged whether a patient corresponding to an alarm/reaction rule is found or not. That is, the alarm generation module 135 frequently monitors the symptom data base 132 and judges whether a patient corresponding to the rule previously stored in the alarm/reaction rule data base 134 is found or not.

When a corresponding patient is found, in S130, a tailored alarm is generated. That is, the alarm generation module 135 transmits information that a health of patient has a problem and information about a reaction that a patient should do. In this case, the corresponding patient can do additional actions according to information included in the alarm information and the actions that the corresponding patient did can be stored in the symptom data base 132 through the individual health record server 120.

As described above, a health care system in accordance with some embodiments of the inventive concept can judge whether a health of patient has a problem or not by applying a different rule to a different patient on the basis of clinical information and health information of each patient. Thus, the health care system in accordance with some embodiments of the invention concept can provide a tailored service to a patient.

FIG. 4 is a block diagram illustrating a health care system 200 in accordance with some other embodiments of the inventive concept. The health care system 200 of FIG. 4 is similar to the health care system 100 of FIG. 1. Referring to FIG. 4, the health care system 200 includes a hospital server 210, an individual health record server 220 and a tailored health care server 230.

Unlike the health care system 100 of FIG. 1, the health care system 200 of FIG. 4 further includes an emergency signal generation module 236. The emergency signal generation module 236 transmits an emergency rescue request to a rescue center server (not shown) when a patient corresponding to the rule stored in the alarm/reaction rule data base 234 is found and an emergency occurs in the corresponding patient. Whether an emergency occurs or not is judged by considering health information additionally measured on the corresponding patient.

Figure 5:
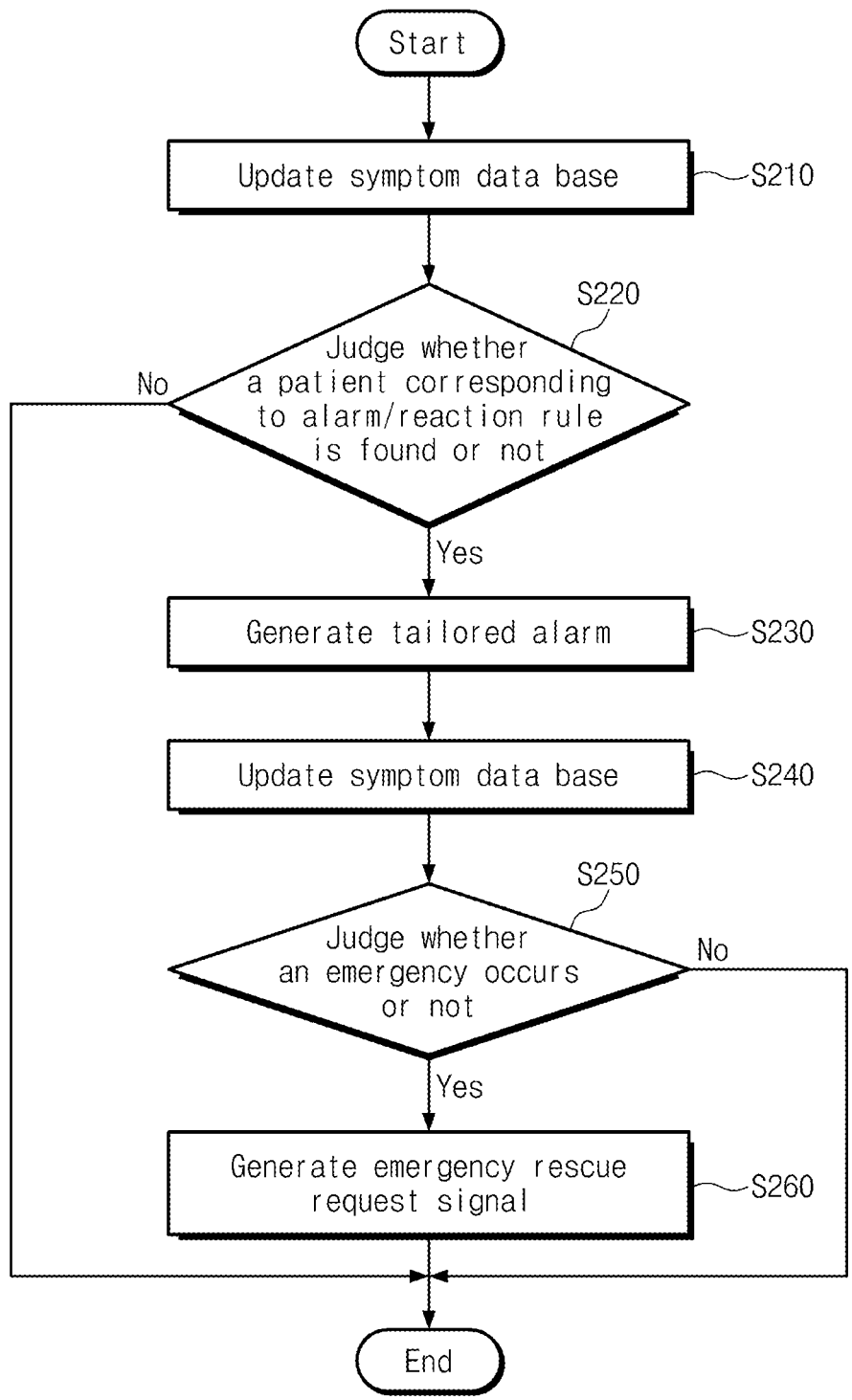
FIG. 5 is a flow chart illustrating an operation of tailored health care server of health care system of FIG. 4.

FIG. 5 is a flow chart illustrating an operation of tailored health care server 230 of health care system 200 of FIG. 4.

In S210, a symptom data base 232 is updated and in S220, an alarm generation module 235 frequently monitors the symptom data base 232 and judges whether a patient corresponding to the rule stored in the alarm/reaction rule data base 234 is found or not.

When the corresponding patient is found, the alarm generation module 235 transmits information that a health of corresponding patient has a problem and information about a reaction that the corresponding patient should do to the patient corresponding to the corresponding rule (S230).

In S240, the symptom data base 232 is updated again. The corresponding patient additionally measures health information using a device after doing an action according to the information about the reaction transmitted by the alarm generation module 135 and the additionally measured health information is stored in a health record data base 121 of the individual health record server 120. The additionally measured health information is stored in the symptom data base 132 through a symptom collection module 131.

In S250, whether an emergency occurs or not is judged. That is, the emergency signal generation module 236 judges whether or not an emergency occurs in the corresponding patient on the basis of information about the alarm transmitted to the corresponding patient and the additionally measured health information. When an emergency occurs, the emergency signal generation module 236 transmits an emergency rescue request signal to a rescue center (S260).

According to the inventive concept, a health care server can provide a different alarm service to a patient having a different health state.

The foregoing is illustrative of the inventive concept and is not to be construed as limiting thereof Although a few embodiments of the inventive concept have been described, those skilled in the art will readily appreciate that many modifications are possible in the embodiments without materially departing from the novel teachings and advantages of the present invention. Accordingly, all such modifications are intended to be included within the scope of the present invention as defined in the claims. The present invention is defined by the following claims, with equivalents of the claims to be included therein.

What is claimed is:

1. A health care server comprising:
an alarm and reaction rule management module generating an alarm rule for a patient on the basis of clinical information of the patient collected from a hospital server and health information of the patient collected from an individual health record server, the health information including information measured by the patient; and
an alarm generation module monitoring clinical information of the patient collected from the hospital server and health information of the patient collected from the individual health record server and generating an alarm when the monitored health information or the clinical information of the patient is found to correspond to the alarm rule generated by the alarm and reaction rule management module, wherein
the alarm rule includes information about an action that the patient can perform, and generating the alarm includes providing the information about the action the patient can perform to the patient.

2. The health care server of claim 1, further comprising:
a symptom collection module collecting clinical information of patient from the hospital server and health information of patient from the individual health care server; and
a symptom data base storing the clinical information and health information collected from the symptom collection module,
wherein the alarm and reaction rule management module generates a different alarm rule to a different patient on the basis of data stored in the symptom data base.

3. The health care server of claim 1, wherein the information measured by the patient includes at least one of information about blood pressure, blood sugar, weight, body temperature, activity, exercise, falling, and taking medicine of the patient.

4. The health care server of claim 1, wherein the clinical information comprises information about one or more of a disease code, a disease classification and a prescription code of the patient.

5. The health care server of claim 1, wherein the health information comprises information measured by one or more of a blood pressure gauge, a blood sugar gauge, a weighing machine, a thermometer, an activity sensor, quantity of motion gauge, a fall sensing device and a taking medicine sensing device.

6. The health care server of claim 1, further comprising an emergency signal generation module judging whether an emergency occurs or not on the basis of the health information added after the alarm is generated.

7. The health care server of claim 1, further comprising a symptom data base storing the clinical information and health information collected by the symptom module, wherein the alarm generation module accesses to the symptom data base at intervals of predetermined time.

8. The health care server of claim 1, further comprising a symptom data base storing the clinical information and health information collected by the symptom module, wherein the alarm generation module accesses to the symptom data base when new clinical information or new health information is additionally input.

9. An operation method of health care server comprising:
storing health information received from an individual health record server of a patient in a symptom data base, the health information including information measured by the patient;
comparing the health information with an alarm rule corresponding to the patient among alarm rules stored in an alarm and reaction rule data base; and
generating an alarm when the health information corresponds to the alarm rule of the patient, wherein
the alarm rule includes information about an action that the patient can perform, and generating the alarm includes providing the information about the action the patient can perform to the patient.

10. The operation method of the health care server of claim 9, wherein the alarm rules are generated on the basis of clinical information collected from a hospital server and the health information collected from the individual health record server, and the alarm rules have a different rule for a different patient.

11. The operation method of health care server of claim 9, further comprising storing health information additionally measured on the patient in the symptom data base after the alarm is generated.

12. The operation method of health care server of claim 11, further comprising judging whether or not an emergency occurs to the patient on the basis of the additionally measured health information stored in the symptom data base.

13. The operation method of health care server of claim 11, wherein the symptom data base stores clinical information of each patient transmitted from a hospital server and health information of each patient transmitted from the individual health record server.

\* \* \* \* \*